(12) United States Patent
Tashiro et al.

(10) Patent No.: US 10,881,600 B2
(45) Date of Patent: Jan. 5, 2021

(54) WATER-BASED COSMETIC AND MANUFACTURING METHOD THEREOF

(71) Applicant: FUJIFILM Corporation, Tokyo (JP)

(72) Inventors: Tomoko Tashiro, Ashigarakami-gun (JP); Yoshisada Nakamura, Ashigarakami-gun (JP); Jun Arakawa, Ashigarakami-gun (JP); Shinichiro Serizawa, Ashigarakami-gun (JP); Hisahiro Mori, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/180,710

(22) Filed: Nov. 5, 2018

(65) Prior Publication Data

US 2019/0070090 A1    Mar. 7, 2019

Related U.S. Application Data

(62) Division of application No. 13/639,561, filed as application No. PCT/JP2011/057260 on Mar. 24, 2011, now abandoned.

(30) Foreign Application Priority Data

Apr. 7, 2010   (JP) ................................ 2010-089059
Mar. 11, 2011  (JP) ................................ 2011-054511

(51) Int. Cl.
| | |
|---|---|
| A61K 8/68 | (2006.01) |
| A61K 8/06 | (2006.01) |
| A61K 8/34 | (2006.01) |
| A61K 8/36 | (2006.01) |
| A61Q 19/00 | (2006.01) |
| A61K 8/39 | (2006.01) |

(52) U.S. Cl.
CPC ................. *A61K 8/68* (2013.01); *A61K 8/06* (2013.01); *A61K 8/345* (2013.01); *A61K 8/361* (2013.01); *A61K 8/39* (2013.01); *A61Q 19/00* (2013.01); *A61K 2800/21* (2013.01)

(58) Field of Classification Search
None
See application file for complete search history.

(56) References Cited

U.S. PATENT DOCUMENTS

| | | |
|---|---|---|
| 5,344,650 A | 9/1994 | Otsuka et al. |
| 2002/0010215 A1 | 1/2002 | Shiroyama et al. |
| 2005/0152865 A1 | 7/2005 | Yamamoto et al. |
| 2005/0287095 A1 | 12/2005 | Fujiwara |
| 2006/0057091 A1 | 3/2006 | Fujii et al. |
| 2009/0197973 A1 | 8/2009 | Arakawa et al. |
| 2010/0015186 A1 | 1/2010 | Takagi et al. |
| 2010/0184733 A1 | 7/2010 | Korevaar et al. |

FOREIGN PATENT DOCUMENTS

| | | | |
|---|---|---|---|
| EP | 1153595 A2 | 11/2001 | |
| FR | 2780886 A1 | 1/2000 | |
| JP | 8-18948 A | 1/1996 | |
| JP | 9-124432 A | 5/1997 | |
| JP | 2001-316217 A | 11/2001 | |
| JP | 2005-2018 A | 1/2005 | |
| JP | 2007-022997 A | 2/2007 | |
| JP | 2008-094810 A | 4/2008 | |
| JP | 2010-505886 A | 2/2010 | |
| JP | 2010-155815 * | 7/2010 | ............... A61K 8/67 |
| JP | 2010-155815 A | 7/2010 | |
| WO | 2006-028311 A1 | 3/2006 | |
| WO | 2009/145299 A1 | 12/2009 | |
| WO | 2010/038815 A1 | 4/2010 | |

OTHER PUBLICATIONS

Machine Translation of JP 2010-155815 (Year: 2010).*
First Office Action, dated Apr. 18, 2013, issued in corresponding CN Application No. 201180016774.8, 9 pages in English and Chinese.
Notice of Reasons for Rejection, dated Apr. 22, 2014, issued in corresponding JP Application No. 2011-054511, 3 pages in English and Japanese.
Notice of Reasons for Rejection, dated Aug. 26, 2014, issued in corresponding JP Application No. 2011-054511, 4 pages in English and Japanese.
New Cosmetics Handbook, Nikko Chemicals Co., Ltd., Oct. 30, 2006, Japan, pp. 95-98.
Communication, dated Oct. 22, 2014, issued in corresponding Ep Application No. 11765430.1, 7 pages in English.
Database WPI, Week 200722, Thomson Scientific London, UK, AN 2007-213668, XP002730714 relating to JP 2007-022997.
Database WPI, Week 200832, Thomson Scientific, London, UK, AN 2008-E68219 XP002730715 related to JP 2008-094810.
Office Action dated Feb. 26, 2016 in the European Application 11765430.1.

(Continued)

*Primary Examiner* — Craig D Ricci
(74) *Attorney, Agent, or Firm* — Sughrue Mion, PLLC

(57) ABSTRACT

A water-based cosmetic that includes: (A) ceramidic compound-containing particles that include a ceramidic compound and that are dispersed as an oil phase in an aqueous phase; (B) a fatty acid component composed of at least one selected from the group consisting of fatty acids and fatty acid salts; and (C) a polyhydric alcohol component that includes a first polyhydric alcohol having an IOB of 2.2 or more and a total content in the composition of from 3% by mass to 20% by mass, and a second polyhydric alcohol having an IOB of 2.0 or less and a total content in the composition of 0% by mass or not more than 3% by mass, wherein a total content of surfactant in the composition is 0% by mass or not more than 1% by mass, and a total mass of ceramidic compound in the composition is at least 3.0 times a total mass of the fatty acid component in the composition.

5 Claims, No Drawings

(56) References Cited

OTHER PUBLICATIONS

International Search Report for National Stage Entry of PCT/JP2011/057260, 2 pages.
PCT/ISA/237 Written opinion for National Stage Entry of PCT/JP2011/057260, 4 pages.

* cited by examiner

WATER-BASED COSMETIC AND MANUFACTURING METHOD THEREOF

CROSS REFERENCE TO RELATED APPLICATIONS

This application is a divisional application of U.S. application Ser. No. 13/639,561 filed Oct. 5, 2012, which is a National Stage of International Application No. PCT/JP2011/057260 filed Mar. 24, 2011, claiming priority based on Japanese Patent Application Nos. 2010-089059 filed Apr. 7, 2010 and 2011-054511 filed Mar. 11, 2011, the contents of all of which are incorporated herein by reference in their entirety.

TECHNICAL FIELD

The present invention relates to a water-based cosmetic and a method of manufacturing the same.

BACKGROUND ART

Ceramides are present in the stratum corneum of the skin, constitute a lipid barrier necessary for water retention, and performs an important role in terms of maintaining water content. There are seven different types of ceramides in the human skin, and their functions are mutually different.

However, ceramides are highly crystalline substances. Therefore, ceramides have low solubility in other oil agents, and it is difficult to ensure stability in the case of adding ceramides to cosmetics due to, for example, precipitation of crystals at low temperatures. Further, although water-based ceramide dispersions can be dispersed using, for example, surfactants, it is difficult to decrease the particle diameter to be sufficiently small, and the resultant dispersions lack clarity in some cases. From such viewpoints, various techniques that provide excellent stability even when ceramides are contained have been developed.

Addition of a specific fatty acid or a specific surfactant is known as a technique for solubilizing ceramidic compounds to become transparent and achieving stable containment thereof, which techniques does not require use of ionic surfactants (see, for example, Japanese Patent Application (JP-A) No. 2001-316217).

Further, Japanese Examined Patent Application Laid-open (JP-B) No. 8-18948 discloses a stable cosmetic having excellent skin moisturizing effect and containing a ceramide, a ceramide saccharide, cholesterol and a cholesterol fatty acid ester.

JP-A No. 2006-312622 discloses a water-in-oil emulsion which contains a ceramidic compound, a predetermined carboxylic acid, a base and a predetermined amount of surfactant, and which is suitable for cosmetics having excellent storage stability and excellent feeling of use even in a case in which the amount of surfactant is small.

However, ceramides are highly crystalline as described above. Therefore, even when a stable emulsion dispersion of ceramides in water is prepared, the dispersion often becomes opaque or often form precipitates in a case in which the dispersion is mixed with general cosmetic ingredients.

Further, even in a case in which ceramidic compounds are used in order to impart functionality such as moisture-retention capacity or barrier function, the permeation properties of ceramidic compounds are still insufficient from the viewpoint of performing the functions.

SUMMARY OF INVENTION

Problem to be Solved by Invention

Therefore, the present invention aims to provide a water-based cosmetic having solution stability and excellent permeation properties, and a method of producing the water-based cosmetic.

Means for Solving the Problem

The present invention includes the following aspects:
[1] A water-based cosmetic including:
 (A) ceramidic compound-containing particles that include a ceramidic compound and that are dispersed as an oil phase in an aqueous phase;
 (B) a fatty acid component composed of at least one selected from the group consisting of fatty acids and fatty acid salts; and
 (C) a polyhydric alcohol component that includes a first polyhydric alcohol having an IOB of 2.2 or more and a total content in the composition of from 3% by mass to 20% by mass, and a second polyhydric alcohol having an IOB of 2.0 or less and a total content in the composition of 0% by mass or not more than 3% by mass,
 wherein a total content of surfactant in the composition is 0% by mass or not more than 1% by mass, and a total mass of the ceramidic compound in the composition is at least 3.0 times a total mass of the fatty acid component.
[2] The water-based cosmetic as described in [1], wherein the first polyhydric alcohol is glycerin, 1,3-butylene glycol or a combination thereof.
[3] The water-based cosmetic as described in [1] or [2], wherein the fatty acid component is at least one selected from the group consisting of fatty acids having from 10 to 30 carbon atoms and fatty acid salts having from 10 to 30 carbon atoms.
[4] The water-based cosmetic as described in any one of [1] to [3], wherein the fatty acid component is at least one selected from the group consisting of lauric acid, isostearic acid, oleic acid, γ-linolenic acid, α-linolenic acid and salts thereof.
[5] The water-based cosmetic as described in any one of [1] to [4], wherein the volume average particle diameter of the ceramidic compound-containing particles is 500 nm or less.
[6] The water-based cosmetic as described in any one of [1] to [5], wherein the surfactant is a nonionic surfactant.
[7] The water-based cosmetic as described in any one of [1] to [6], wherein the IOB of the second polyhydric alcohol contained in the water-based cosmetic is from 1.0 to 2.0.
[8] The water-based cosmetic as described in any one of [1] to [7], wherein a content of the second polyhydric alcohol is not more than 80% by mass of a total content of the first polyhydric alcohol.
[9] A method of producing the water-based cosmetic of any one of [1] to [8], including:
 mixing an oil phase component that includes at least a ceramidic compound, and an aqueous phase component, at a temperature of 40° C. or lower, to obtain a ceramide dispersion that includes a polyhydric alcohol component in the aqueous phase component; and
 mixing the ceramide dispersion and an aqueous composition.
[10] The method of producing the water-based cosmetic as described in [9], wherein the polyhydric alcohol component is added as one component in the aqueous phase component when the oil phase component and the aqueous phase component are mixed, or the polyhydric alcohol component is added to the ceramide dispersion liquid obtained after the mixing.

[11] The method of producing the water-based cosmetic as described in [9] or [10], including dissolving the ceramidic compound in a good solvent for ceramides.

[12] The method of producing the water-based cosmetic as described in any one of [9] to [11], wherein the oil phase component and the aqueous phase component are each independently passed through a microchannel of which a cross-sectional area of a narrowest part thereof is from 1 $\mu m^2$ to 1 $mm^2$, and are thereafter combined and mixed with each other.

Advantageous Effect of Invention

According to the invention, a water-based cosmetic having solution stability and excellent permeation properties, and a method of producing the water-based cosmetic, can be provided.

BEST EMBODIMENT FOR CARRYING OUT INVENTION

The water-based cosmetic of the invention is a water-based cosmetic including:

(A) ceramidic compound-containing particles that include a ceramidic compound and that are dispersed as an oil phase in an aqueous phase;

(B) a fatty acid component composed of at least one selected from the group consisting of fatty acids and fatty acid salts; and (C) a polyhydric alcohol component that includes a first polyhydric alcohol having an IOB of 2.2 or more and a total content in the composition of from 3% by mass to 20% by mass, and a second polyhydric alcohol having an IOB of 2.0 or less and a total content in the composition of 0% by mass or not more than 3% by mass;

wherein a total content of surfactant in the composition is 0% by mass or not more than 1% by mass, and a total mass of the ceramidic compound in the composition is at least 3.0 times a total mass of the fatty acid component.

According to the invention, the water-based cosmetic includes a polyhydric alcohol component that includes two types of polyhydric alcohols, which are distinguished from each other based on IOB, in respectively specified amounts, and a specified fatty acid component. Therefore, the permeation properties of the ceramidic compound, which is a functional component, can be heightened, and the occurrence of aggregation of ceramidic compound-containing particles can be suppressed, as a result of which excellent solution stability can be achieved.

In the invention, the term "aqueous phase" is used as a term contrasting with "oil phase", regardless of the type of solvent.

In the present specification, the term "process" encompasses an independent process, as well as a process that cannot be clearly distinguished from another process but yet achieves the expected effect of the process of interest.

In the present specification, any numerical range expressed herein using "to" refers to a range including the numerical values before and after "to" as the minimum and maximum values, respectively.

In a case in which the amount of a component in the composition is indicated in the invention, when there are plural substances corresponding to the component in the composition, the indicated amount means the total amount of the plural substances present in the composition, unless specifically stated otherwise.

The invention is described below.

1-1. Ceramidic Compound-Containing Particles

The ceramidic compound-containing particles in the invention are particles that include at least a ceramidic compound, and that are dispersed, as an oil phase (oil droplets), in an aqueous phase.

The ceramidic compound in the invention encompasses ceramides and derivatives thereof, and may have any origin such as a synthetic product or an extract. The "ceramidic compound" in the invention encompasses the below-described natural ceramides and compounds having natural ceramides as basic skeletons, and precursor substances from which these compounds can be derived, and the "ceramidic compound" is a generic term for natural ceramides, glycosylated ceramides such as sphingoglycolipids, synthetic ceramides, sphingosine and phytosphingosine, and derivatives thereof. In the following, the ceramidic compound in the invention is described in detail.

(Natural Ceramide)

In the invention, a natural ceramide refers to a ceramide having the same structure as that present in the stratum corneum of the human skin. A more preferred embodiment of the natural ceramide is an embodiment in which the natural ceramide has three or more hydroxyl groups in its molecular structure, and does not include a sphingoglycolipid.

Natural ceramides that can be used in the invention are described in detail below.

Examples of natural ceramides that can preferably be used in the invention include ceramide 1, ceramide 9, ceramide 4, ceramide 2, ceramide 3, ceramide 5, ceramide 6, ceramide 7, ceramide 8 and ceramide 3B.

Further, compounds obtained by subjecting the ceramidic compounds to modifications in accordance with the purpose, such as introduction of a double bond into the molecule in order to impart solubility or introduction of a hydrophobic group in order to impart permeation properties, can also be used.

Ceramides having a general structure referred to as natural type are natural products (extracts) or obtained by microbial fermentation methods, and may further include synthetic ceramides or animal-derived ceramides.

Naturally-occurring optical isomers (D (−) form) may be used as these ceramides. Alternatively, non-naturally occurring optical isomers (L (+) form) may be used in accordance with the necessity, and it is also possible to use a mixture of naturally-occurring and non-naturally occurring optical isomers. The relative steric configuration of the compound may be a naturally-occurring steric configuration, or a non-naturally occurring steric configuration other than the naturally-occurring steric configuration, or a mixture thereof.

In a case in which the water-based cosmetic of the invention is used for the purpose of, for example, a skin emollient, the proportion of naturally-occurring optical isomers is preferably higher from the viewpoint of barrier effect.

Natural ceramides are also available as commercial products, and examples thereof include Ceramide I, Ceramide III, Ceramide IIIA, Ceramide IIIB, Ceramide IIIC, and Ceramide VI (manufactured by Cosmofarm), Ceramide TIC-001 (manufactured by Takasago International Corporation), CERAMIDE II (manufactured by Quest International), DS-Ceramide VI, DS-CLA-Phytoceramide, C6-Phytoceramide, DS-ceramide Y3S (manufactured by Doosan Biotech Co., Ltd.), CERAMIDE2 (manufactured by Sederma), etc. Exemplary Compound (1-5) shown above is available as "Ceramide 3" (tradename, manufactured by Evonik Industries (formally, Degussa Corporation), and Exemplary Compound (1-7) shown above is available as "Ceramide 6" (tradename, manufactured by Evonik Industries (formally, Degussa Corporation).

The ceramidic compound-containing particles may include one natural ceramide, or two or more natural ceramides in combination. Since ceramidic compounds generally have high melting points and are highly crystalline, combined use of two or more natural ceramides is preferable in terms of emulsion stability and handling properties.

(Glycosylated Ceramide)

A glycosylated ceramide is a ceramide compound containing a saccharide in a molecule thereof. Examples of the saccharide contained in the molecule of this ceramide compound include monosaccharides such as glucose and galactose, disaccharides such as lactose and maltose, and oligosaccharides and polysaccharides which are obtained by polymerization of such monosaccharides or disaccharides through glycosidic bonding. The saccharide may be a sugar derivative obtained by replacing a hydroxyl group or hydroxyl groups of a sugar unit with another group or groups. Examples of the sugar derivative include glucosamine, glucuronic acid, N-acetylglucosamine, etc. In particular, from the viewpoint of dispersion stability, saccharides having from 1 to 5 sugar units are preferable, and, specifically, glucose and lactose are preferable, and glucose is more preferable.

Specific examples of glycosylated ceramides include those shown below.

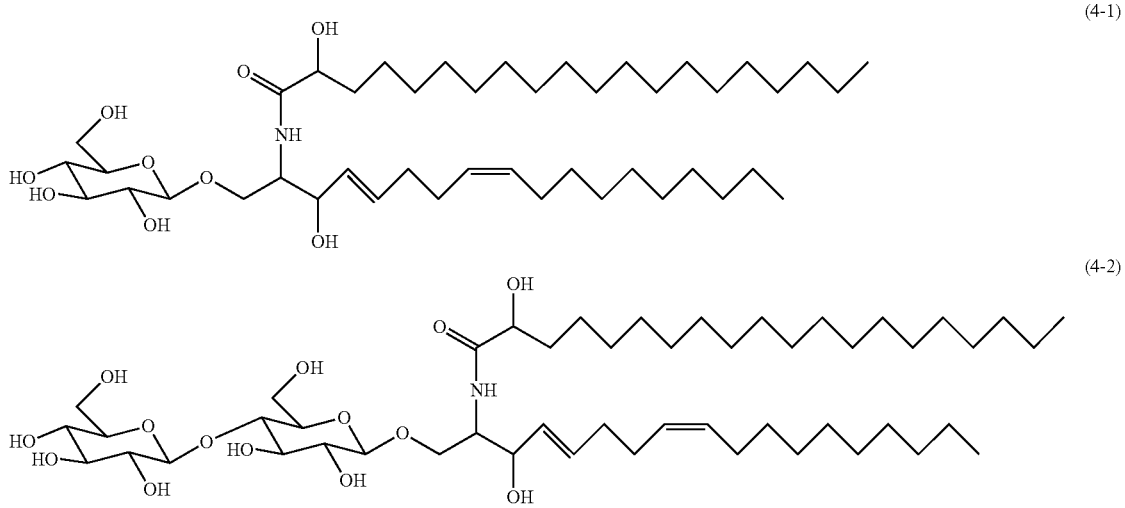

Glycosylated ceramides can be obtained by synthesis, or as commercial products. For example, Exemplary Compound (4-1) shown above is available as "Kone-sphingo-toushishitsu" (rice sphingoglycolipid) (tradename, manufactured by Okayasu Shoten Co., Ltd.).

(Synthetic Ceramide)

Ceramide analogues are compounds synthesized to mimic the structures of ceramides. Known compounds of such synthetic ceramides include synthetic ceramides (3-1) and (3-2) represented by the following structural formulae.

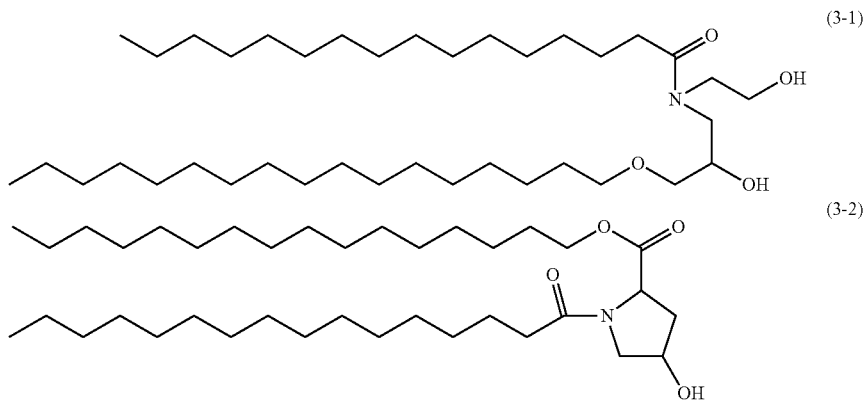

In a case in which a synthetic ceramide is applied, for example, the synthetic ceramide is preferably a synthetic ceramide synthesized to mimic the structure of a natural ceramide or a glycosylated ceramide, and more preferably a synthetic ceramide synthesized to mimic the structure of a natural ceramide, from the viewpoint of the feeling of use and moisturized feeling of the water-based cosmetic of the invention. Synthetic ceramides are also available as commercial products. For example, Exemplary Compound (3-2) shown above (cetylhydroxyproline palmitamide) is available as "CeramideBio" (tradename, manufactured by symrise AG).

(Sphingosine, Phytosphingosine)

Sphingosines and phytosphingosines that can be used may be synthetic products or natural products, and include natural sphingosines and sphingosine analogues.

Specific examples of natural sphingosines include sphingosine, dihydrosphingosine, phytosphingosine, sphingadienine, dehydrosphingosine, dehydrophitosphingosine, and N-alkylated bodies (for example, N-methylated bodies) thereof and acetylated bodies of thereof.

The sphingosine to be used may be a naturally-occurring (D (−) form) optical isomer or a non-naturally occurring (L (+) form) optical isomer, or a mixture of the naturally-occurring optical isomer and the non-naturally occurring optical isomer. The relative steric configuration of the compound may be a naturally-occurring steric configuration, or a non-naturally occurring steric configuration other than the naturally-occurring steric configuration, or a mixture thereof. Specific examples thereof include PHYTOSPHINGOSINE (INCI name; 8th edition) and exemplary compounds shown below.

(5-1)

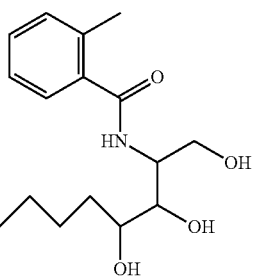

(5-2)

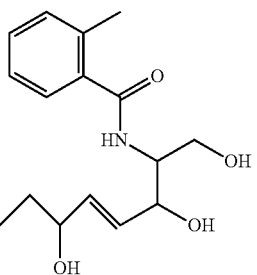

(5-3)

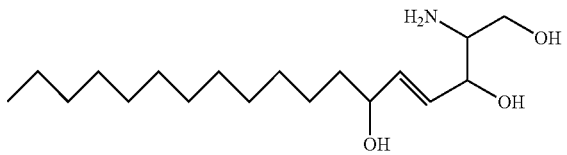

(5-4)

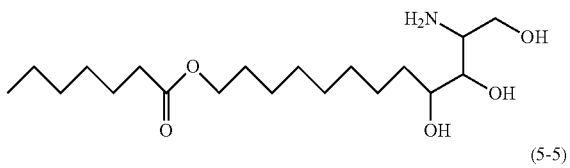

(5-5)

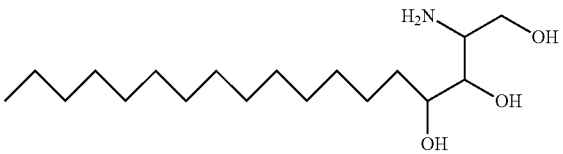

The phytosphingosine to be used may be a natural extract or a synthetic product, and can be obtained by synthesis or as a commercial product.

Commercial products of natural sphingosines include D-Sphingosine (4-Sphingenine) (manufactured by SIGMA-ALDRICH), DSphytosphingo sine (manufactured by Doosan Biotech Co., Ltd.) and phytosphingosine (manufactured by Cosmofarm), and Exemplary Compound (5-5) shown above is available as "phytosphingosine" (tradename, manufactured by Evonik Industries (formally, Degussa Corporation)).

(Acid)

In the invention, in the case of using a sphingosine compound such as sphingosine or phytosphingosine, the sphingosine compound is preferably used in combination with a compound that has an acidic residue capable of forming a salt with the sphingosine compound. The compound having the acidic residue is preferably an inorganic acid or an organic acid having 5 or fewer carbon atoms.

Examples of the inorganic acid include phosphoric acid, hydrochloric acid, nitric acid, sulfuric acid, perchloric acid, carbonic acid, etc. Phosphoric acid and hydrochloric acid are preferable.

Examples of the organic acid include: monocarboxylic acids such as formic acid, acetic acid, propionic acid, butyric acid, isobutyric acid and valeric acid; dicarboxylic acids such as succinic acid, phthalic acid, fumaric acid, oxalic acid, malonic acid and glutaric acid; oxycarboxylic acids such as glycolic acid, citric acid, lactic acid, pyruvic acid, malic acid and tartaric acid; and amino acids such as glutamic acid and aspartic acid. Among these compounds, phosphoric acid, hydrochloric acid, succinic acid, citric acid, lactic acid, glutamic acid, aspartic acid, etc. are preferable, and lactic acid, glutamic acid, aspartic acid, etc. are particularly preferable.

The acid to be used in combination with the sphingosine compound may be mixed with the sphingosine compound in advance before use, or added at the time of forming the ceramide analogue-containing particles, or added as a pH adjuster after forming the ceramidic compound-containing particles.

In a case in which an acid is used in combination with the sphingosine compound, the addition amount of the acid is preferably from about 1 part by mass to about 50 parts by mass relative to 100 parts by mass of the sphingosine compound to be used.

(Content of Ceramidic Compound)

The content of ceramidic compounds is preferably from 20% by mass to 100% by mass, and more preferably from 30% by mass to 100% by mass, relative to the total mass of oil components contained in the oil phase in the ceramidic compound-containing particles, from the viewpoint of efficient skin absorption of ceramide components and effects that are expected to be exerted by ceramides in the case of using the water-based cosmetic of the invention. The proportion of natural ceramides relative to the total mass of ceramidic compounds is preferably 30% by mass or higher from the viewpoint of effects expected to be exerted by natural ceramides, and is most preferably 100% by mass.

The content of ceramidic compounds in the water-based cosmetic of the invention is preferably in a range of from 0.001% by mass to 5% by mass, and more preferably from 0.01% by mass to 3% by mass. As a result of the inclusion of ceramidic compounds in the above-described range in the water-based cosmetic of the invention, the water-retention capacity and barrier function recovery effect of the water-based cosmetic of the invention can be obtained.

(Particle Diameter of Ceramidic Compound-Containing Particles)

The volume average particle diameter of the ceramidic compound-containing particles is preferably 500 nm or less, more preferably from 2 nm to 150 nm, still more preferably from 3 nm to 150 nm, and further preferably from 5 nm to 120 nm, and most preferably from 5 nm to 100 nm, from the viewpoint of the stability and skin permeation properties of the ceramidic compound-containing particles.

The particle diameter of the dispersed particles in the invention can be measured using various commercially available particle size analyzers. However, the dynamic light scattering method is applied due to the particle size range and ease of measurement thereof.

Examples of commercially available measurement instruments using dynamic light scattering include Nanotrac UPA (manufactured by Nikkiso Co., Ltd.), a dynamic light scattering particle size analyzer LB-550 (manufactured by HORIBA Ltd.), and a concentrated-system particle diameter analyzer FPAR-1000 (manufactured by Otsuka Electronics Co., Ltd.).

The particle diameter of the dispersed particles in the invention is a value obtained by measurement using a dynamic light scattering particle size analyzer LB-550 (manufactured by Horiba Seisakusho Co., Ltd.), and, specifically, the value measured as described below is adopted.

For the measuring method of the particle diameter, dilution is carried out with pure water such that the concentration of oil components contained in a sample sampled from the emulsion of the invention becomes 1% by mass, and measurement is carried out using a quartz cell. The particle diameter can be determined as a volume average diameter obtained with the settings in which the refractive index of the sample is set at 1,600, the refractive index of the dispersion medium is set at 1.333 (pure water), and the viscosity of the dispersion medium is set at the viscosity of pure water.

The manner in which the ceramidic compound-containing particles are formed may be 1) a manner in which the ceramidic compound-containing particles (oil phase) are formed as solid particles in advance, and then dispersed in a dispersion medium (aqueous phase), or 2) a manner in which a ceramidic compound is converted to a melted state by heating or converted to a liquid state by being dissolved in an appropriate solvent, and then added to an aqueous phase and dispersed, and then the temperature is decreased to normal temperature or the solvent is removed, to form ceramidic compound-containing particles in the system. For the preparation, natural ceramides etc. are preferably mutually dissolved with another oil component or dissolved in an organic solvent.

(Another Oil Component)

The water-based cosmetic of the invention is configured such that ceramidic compound-containing particles as an oil phase are dispersed in an aqueous phase. In an configuration, an oil component (sometimes referred to as "another oil component" in the present specification) other than ceramidic compounds (e.g., natural ceramides) and/or a solvent may also be contained in the oil phase, such that natural ceramide-containing dispersed particles in the form of oil droplets are present, as natural ceramidic compound-containing particles, in the oil component and/or solvent. In a case in which this configuration is adopted, the average particle diameter of the ceramidic compound-containing particles in the invention refers to the average particle diameter of the dispersed particles in the form of oil droplets which contain ceramidic compound-containing particles.

In the invention, the "another oil component (other oil components)" refers to an oil component that does not separate from the ceramidic compound at normal temperature, and the "solvent" refers to a solvent capable of dissolving the ceramidic compound. Examples of the solvent include alcohols.

Here, another oil component that can be used together with the ceramidic compound is not particularly limited, and may be, for example, an oil component as an active ingredient that is added in accordance with the purpose of use of the water-based cosmetic, or an oil component that is used for the purpose of improving the dispersion stability or the feeling of use on the skin or of controlling the properties of the water-based cosmetic. In the following, another oil component that can be used in the invention is described. The fatty acid having from 10 to 30 carbon atoms as referred to in the "(2) fatty acid having from 10 to 30 carbon atoms or a salt thereof" in the invention may be contained, as another oil component, in the ceramide-containing particles. The details of the fatty acid having from 10 to 30 carbon atoms or salt thereof are described later.

(Oil Component as Active Ingredient)

In the invention, a functional ingredient for cosmetics that is insoluble or hardly soluble in an aqueous medium (particularly, water) is preferably contained as an oil component. Inclusion of a functional oil component, such as the later-described carotenoid, in the water-based cosmetic of the invention provides the water-based cosmetic of the invention with an excellent emollient effect, a skin aging preventive effect or an antioxidant effect.

The "functional ingredient" as used in the present specification means a component that can be expected to induce a predetermined physiological effect in the living organism to which the functional ingredient is applied.

The oil component that can be used in the invention is not particularly limited as long as it is a component that dissolves in an oil medium but is insoluble or hardly soluble in an aqueous medium (particularly, water). Radical scavengers including oil-soluble vitamins such as carotenoids and tocopherols, and fatty substances such as coconut oil, are preferably used as oil components.

The expression "insoluble in an aqueous medium" means that the solubility in 100 mL of the aqueous medium is 0.01 g or less at 25° C., and the expression "hardly soluble in an aqueous medium" means that the solubility in 100 mL of the aqueous medium is from more than 0.01 g to 0.1 g at 25° C.

Carotenoids

Carotenoids containing natural colorants can preferably be used as oil components that serve as active ingredients.

Carotenoids that can be used in the water-based cosmetic of the invention are yellow to orange terpenoid colorants, and include those of natural products such as plants, algae and bacteria.

Carotenoids in the invention are not limited to naturally-derived carotenoids, and include any carotenoids that are obtained according to ordinary methods. For example, many of the carotenes of the later-described carotenoids are produced also by synthesis, and many of commercially available β-carotenes are produced by synthesis.

Examples of carotenoids include hydrocarbons (carotenes) and oxidized alcohol derivatives thereof (xanthophylls).

Examples of carotenoids include actinioerythrol, bixin, canthaxanthin, capsanthin, capsorubin, β-8'-apo-carotenal (apocarotenal), β-12'-apo-carotenal, α-carotene, β-carotene, "carotene" (mixture of α- and β-carotenes), γ-carotene, β-cryptoxanthin, lutein, lycopene, violaxanthin, and zeaxanthin, and esters of hydroxyl- or carboxyl-containing carotenoids selected therefrom.

Although many cartenoids are present in the form of cis and trans isomers in the nature, synthetic products are often cis-trans mixtures.

Cartenoids can generally be extracted from plant materials. Such cartenoids have various functions and, for example, lutein extracted from petals of *Tagetes* genus is used widely as a raw material for fowl feeds and has a function of coloring skins and fats of fowls and eggs laid by fowls.

The carotenoids may be contained in ceramidic compound-containing particles. Alternatively, the carotenoids may be contained s in the water-based cosmetic separately from the ceramidic compound-containing particles.

Fatty Substances

Examples of fatty substance that may be used as another oil component include fatty substances (fatty oils) that are liquid at normal temperature and fatty substances (fats) that are solid at normal temperature.

Examples of the liquid fatty substances include olive oil, camellian oil, macadamia nuts oil, castor oil, avocado oil, evening primrose oil, turtle oil, corn oil, mink oil, rapeseed oil, yolk oil, sesame oil, persic oil, wheat germ oil, sasanqua oil, linseed oil, cotton seed oil, perilla oil, soybean oil, peanut oil, tea seed oil, kaya oil, rice bran oil, Chinese tung oil, Japanese tung oil, jojoba oil, germ oil, triglycerin, glycerin trioctanoate, glycerin triisopaltimate, salad oil, safflower oil (Carthamus tinctrious oil), palm oil, coconut oil, peanut oil, almond oil, hazelnut oil, walnut oil, grape seed oil, etc.

Examples of the solid fatty substances include beef tallow, hydrogenated beef tallow, neat's-foot tallow, beef bone tallow, mink oil, egg yolk oil, lard, horse fat, mutton tallow, hydrogenated oil, cacao fat, coconut oil, hydrogenated coconut oil, palm oil, hydrogenated palm oil, Japan wax, Japan wax kernel oil, hydrogenated castor oil, etc.

Among them, coconut oil, which is a medium chain fatty acid triglyceride, is preferably used from viewpoints of the diameters of dispersed particles and the stability in the water-based cosmetic.

In the invention, commercial products may be used as the fatty substances. In the invention, the fatty substance may be used singly, or in mixture.

Examples of a compounds having a phenolic hydroxyl group as another oil component that can be used in the invention include polyphenols (such as catechin), guaiac gum, nordihydroguaiaretic acid (NDGA), gallate esters, BHT (butyl hydroxy toluene), BHA (butyl hydroxy anisol), vitamins E, bisphenols, etc. Examples of the gallate esters include propyl gallate, butyl gallate and octyl gallate.

Examples of amine-based compounds include phenylene diamine, diphenyl-p-phenylene diamine or 4-amino-p-diphenylamine. Diphenyl-p-phenylene diamine or 4-amino-p-diphenylamine is more preferable.

Oil-solubilized derivatives of ascorbic acid and erhthorbic acid include L-ascorbyl stearate, L-ascorbyl tetraisopalmitate, L-ascorbyl palmitate, erythorbyl palmitate, erythorbyl tetraisopalmitate, etc.

Among those listed above, vitamins E are preferable due to their high safety and antioxidant function.

Vitamins E are not particularly limited, and examples thereof include those selected from a group of compounds consisting of tocopherols and derivatives thereof, and a group of compounds consisting of tocotrienols and derivatives thereof. These may be used singly, or in combination of two or more thereof. It is also possible to use a compound selected from the group of compounds consisting of tocopherols and derivatives thereof, and a compound selected from the group of compounds consisting of tocotrienols and derivatives thereof, in combination.

The group of compounds consisting of tocopherols and derivatives thereof include dl-α-tocopherol, dl-β-tocopherol, dl-γ-tocopherol, dl-δ-tocopherol, acetic acid-dl-α-tocopherol, nicotinic acid-dl-α-tocopherol, linoleic acid-dl-α-tocopherol and succinic acid-dl-α-tocopherol. Among these, dl-α-tocopherol, dl-β-tocopherol, dl-γ-tocopherol, dl-δ-tocopherol and mixtures thereof (mixed tocopherols) are more preferable. Acetic esters of these compounds are preferably used as tocopherol derivatives.

The group of compounds consisting of tocotrienols and derivatives thereof include α-tocotrienol, β-tocotrienol, γ-tocotrienol, δ-tocotrienol, etc. Acetic esters of these compounds are preferably used as tocotrienol derivatives. Tocotrienols are tocopherol analogues contained in wheat, rice bran, palm oil, etc., and each have three double bonds in the side chain of tocopherol, and exhibit excellent antioxidant activity.

These vitamins E are preferably contained as oil-soluble antioxidants in, particularly, the oil phase of the water-based cosmetic, since the antioxidant activity toward oil components can effectively be exerted. Among the vitamins E, it is more preferable that at least one selected from the group of compounds consisting of tocotorienols and derivatives thereof is contained, from the viewpoint of antioxidant effect.

The contents of other oil components, such as carotenoids and fatty substances, discussed above can be set, as appropriate, in accordance with the formulation of the water-based cosmetic of the invention.

1-2. Fatty Acid Having from 10 to 30 Carbon Atoms or Salt Thereof

The water-based cosmetic of the invention includes a fatty acid having from 10 to 30 carbon atoms or a salt thereof (hereinafter sometimes collectively referred to as "fatty acid component"). The fatty acid component enhances the permeation properties of ceramidic compounds. Further, the fatty acid component easily dissolves in the system during a step of mixing the oil phase and the aqueous phase in the preparation of the water-based cosmetic. Therefore, the dispersion stability of fine ceramidic compound-containing particles contained in the water-based cosmetic can be made excellent, and the transparency of the water-based cosmetic is not impaired.

In a case in which a fatty acid having from 10 to 30 carbon atoms is applied as a fatty acid component, the fatty acid is preferably contained as an oil phase component in the water-based cosmetic, and preferably contained as a component of the ceramide-containing particles.

In a case in which a salt (fatty acid salt) of a fatty acid having from 10 to 30 carbon atoms is applied as a fatty acid component, the fatty acid salt is soluble in aqueous media, and thus can be a water-phase component of the water-based cosmetic. A fatty acid having from 10 to 30 carbon atoms or a salt thereof may be contained singly as a fatty acid component in the invention, or a fatty acid having from 10 to 30 carbon atoms and a salt thereof may be used in combination.

The fatty acid having from 10 to 30 carbon atoms may be a saturated or unsaturated fatty acid. From the viewpoint of emulsion and dispersion stability, the fatty acid having from 10 to 30 carbon atoms is preferably a fatty acid that is liquid at or near the room temperature, for example, at 30° C.

Specific examples of the fatty acid component for the invention include capric acid, lauric acid, myristic acid, palmitic acid, palmitoleic acid, stearic acid, oleic acid, 12-hydroxy stearic acid, undecylenic acid, tolic acid, isostearic acid, arachidic acid, behenic acid, linolic acid, α-linolenic acid, γ-linolenic acid, arachidonic acid, docosahexaenoic acid (DHA), eicosapentaenoic acid (EPA), erucic acid, etc., and salts thereof. These substances may be used singly or in combination of two or more thereof. From the viewpoints of color, smell and skin irritation, the fatty acid component in the invention is preferably at least one selected from the group consisting of lauric acid, isostearic acid, oleic acid, γ-linolenic acid, α-linolenic acid and salts thereof, and is particularly preferably oleic acid.

In a case in which a fatty acid salt is employed as a fatty acid component, the salt structure of the fatty acid salt may be a salt of a metal such as sodium or potassium, a salt of a basic amino acid such as L-arginine, L-histidine or L-lysine, and an alkanolamine salt such as triethanolamine. The type of salt is suitably selected in accordance with the type of fatty acid to be used. Metal salts such as sodium salts are preferable from the viewpoint of solubility and dispersibility.

In the water-based cosmetic of the invention, the ceramidic compound is dispersed using a fatty acid component in place of an emulsifying agent such as a surfactant. Therefore, the permeation of the ceramidic compound into the stratum corneum is enhanced, as compared to a case in which an emulsifying agent such as a surfactant is used. In the water-based cosmetic, the fatty acid component may be contained in any amount that allows the ceramidic compound to be dispersed well. The total mass of ceramidic compounds in the composition is preferably at least 3.0 times the total mass of fatty acid component, more preferably from 3.0 times to 100 times the total mass of fatty acid component, and still more preferably from 4.0 times to 20 times the total mass of fatty acid component, from the viewpoint of storage stability and permeation properties. Separation and precipitation of excessive fatty acids are suppressed by setting the amount of ceramidic compounds to be at least 3.0 times that of the fatty acid component, and, therefore, such a ceramidic compound amount is preferable. By setting the amount of ceramidic compounds to be not more than 100 times the amount of fatty acid components, fixation onto the ceramidic compounds is sufficient, and, therefore, such a ceramidic compound amount is preferable.

From the viewpoint of the transparency of the water-based cosmetic, the content of fatty acid component is preferably from 0.00001% by mass to 3.0% by mass of the total mass of the water-based cosmetic, and more preferably from 0.00005% by mass to 2.0% by mass of the total mass of the water-based cosmetic.

1-3. Polyhydric Alcohol Component

The polyhydric alcohol component in the water-based cosmetic of the invention includes a first polyhydric alcohol having an IOB of 2.2 or more and a total content in the composition of from 3% by mass to 20% by mass, and a second polyhydric alcohol having an IOB of 2.0 or less and a total content in the composition of 0% by mass or not more than 3% by mass. In the invention, from among the two types of polyhydric alcohol components having different IOBs, the first polyhydric alcohol having a higher IOB is contained in a larger amount than that of the second polyhydric alcohol having a lower IOB, as a result of which the occurrence of aggregation of ceramidic compound-containing particles is effectively prevented, and the solution stability becomes excellent.

In the invention, the term "polyhydric alcohol" refers to a substance that has two or more hydroxyl groups in the compound, and that is liquid at 25° C.

Here, IOB (Inorganic Organic Balance) is well known, and represents a ratio between an inorganic value and an organic value determined based on the organic conceptual diagram. IOB indicates the degree of polarity of an oily base, and is represented by Formula (I) shown below. Specifically, IOB is determined by the following Formula (I) in accordance with Fujita, "*Yuuki-kagoubutsu-no-yosoku-to-yuuki-gainennzu*" (Prediction of Organic Compounds and Organic Conceptual Diagram), (Kagaku-no-ryouiki (Chemical Field) 11-10, 1957), pp. 719-725; Yaguchi, "*Yuukigainennzu-niyoru-nyuuka-shohou-sekkei*" (Emulsion Formulation Design by Organic Conceptual Diagram), (Nihon Emulsion Co., Ltd., 1985), p. 98.

$$\text{IOB} = \text{Inorganic Value (IV)}/\text{Organic Value (OV)} \quad (I)$$

In the invention, the first polyhydric alcohol has an IOB of 2.2 or greater. Examples of the first polyhydric alcohol include propylene glycol (IOB=3.33), glycerin (IOB=5.00), 1,3-butyleneglyco-diglycerin (IOB=3.5), etc., or any combination of two or more thereof.

Among them, polyhydric alcohols having IOBs of 2.4 or greater are preferable, polyhydric alcohols having IOBs of 2.8 or greater are more preferable, polyhydric alcohols having IOBs of 3.2 or greater are most preferable, and glycerin is particularly preferable, from the viewpoint of particle stability.

The second polyhydric alcohol has an IOB of 2.0 or smaller. Examples of the second polyhydric alcohol include isoprene glycol (IOB=2.00), dipropylene glycol (IOB=1.83), ethoxy diglycol (diethylene glycol monoethyl ether) (IOB=1.63), penthylene glycol (IOB=2.00), hexylene glycol (IOB=1.82), etc., or any combination of two or more thereof.

The second polyhydric alcohol contained in the water-based cosmetic of the invention preferably has an IOB of from 1.0 to 2.0, and most preferably has an IOB of from 1.5 to 2.0, from the viewpoint of particle stability.

The content of the first polyhydric alcohol in the water-based cosmetic is from 3% by mass to 20% by mass. In a case in which the content of the first polyhydric alcohol is 3% by mass or lower, moisture retention effect exerted by the first polyhydric alcohol cannot be expected. Further, a content of the first polyhydric alcohol of 20% by mass or higher deteriorates the particle stability and lowers the transparency, and, therefore, is not preferable. The content of the first polyhydric alcohol is more preferably from 5.0% by mass to 15.0% by mass.

The content of the second polyhydric alcohol in the water-based cosmetic is 3% by mass or lower. A content of the second polyhydric alcohol of 3% by mass or lower does not impair the solution stability of the water-based cosmetic. The content of the second polyhydric alcohol is preferably from 0.0% by mass to 2.0% by mass, more preferably from 0.0% by mass to 1.0% by mass, and particularly preferably 0 (i.e., the second alcohol is not contained in the water-based cosmetic), from the viewpoint of particle stability.

The content of the second polyhydric alcohol is preferably not more than 80% by mass of the total content of the first polyhydric alcohol, and more preferably not more than 50% by mass of the total content of the first polyhydric alcohol, and particularly preferably 0, from the viewpoint of solution stability.

The content of the first polyhydric alcohol in the water-based cosmetic is preferably from 3 to 1,000 times the total mass of ceramidic compounds, more preferably from 5 to 1,000 times the total mass of ceramidic compounds, and more preferably 10 to 1,000 times the total mass of ceramidic compounds, from the viewpoint of imparting stability and moisture retention capacity.

The polyhydric alcohol generally has a moisture retention function, a viscosity adjustment function, etc., and also has functions of decreasing the interfacail tension between water and an oil component, facilitating expansion of the interface, and facilitating the formation of fine particles. Therefore, the particle diameters of dispersed particles contained in the water-based cosmetic can be made smaller. The addition of polyhydric alcohol can also decrease the water activity of the water-based cosmetic, and suppress the proliferation of microorganisms.

In consideration of the above, besides the first polyhydric alcohol and the second polyhydric alcohol, a third polyhydric alcohol having an IOB of from more than 2.0 to less than 2.2 may be contained as a polyhydric alcohol component within a range in which the effect of the invention is not hindered.

Any di- or higher-hydric alcohol can be used as the third polyhydric alcohol optionally employed in the invention, without particular restriction.

The polyhydric alcohol employed as a polyhydric alcohol component preferably has three or more hydroxyl groups in one molecule thereof. This structure more effectively decreases the interfacial tension between the aqueous medium and the fatty component, thereby allowing formation of finer and more stable fine particles. As a result, in the case of applying the water-based cosmetic of the invention to the skin, for example, the skin permeation properties can be heightened.

The total content of polyhydric alcohol component is not particularly limited as long as the total content is 3% by mass or higher relative to the total mass of the water-based cosmetic. The total content is preferably 20% by mass or lower, more preferably from 3% by mass to 18% by mass, and still more preferably from 3% by mass to 15% by mass, relative to the total mass of the water-based cosmetic, from the viewpoint of suppressing stinging (tingling sensation on the skin).

In a case in which the polyhydric alcohol component is configured to include the third polyhydric alcohol, the content of the first polyhydric alcohol in the polyhydric alcohol component is preferably 50% by mass or higher, more preferably 80% by mass or higher, and particularly preferably 100% by mass, relative to the total mass of the polyhydric alcohol component, from the viewpoint of sufficiently obtaining the effect exerted by the first polyhydric alcohol.

1-4. Surfactant

The water-based cosmetic of the invention may include a surfactant. The scope of surfactant does not encompass the fatty acid component described above. The content of surfactant is 0, or is not more than 1% by mass of the total mass of the water-based cosmetic. From the viewpoint of transparency and stability of the water-based cosmetic, the content of ionic surfactant, particularly, nonionic surfactant, in the water-based cosmetic may be from 10 to 100 times the total mass of ceramidic compounds.

The surfactant, other than fatty acid components, in the invention may be any of cationic, anionic, amphoteric and nonionic surfactants.

Examples of ionic surfactants include alkylsulfonic acid salts, alkyl sulfate salts, monoalkyl phosphate salts, lecithin, etc. Sodium chloride, sodium citrate, sodium ascorbate, etc. are used as salts.

The content of these ionic surfactants is preferably not more than 0.1 times the total mass of oil components, and it is more preferable that the water-based cosmetic does not contain any ionic surfactant, in consideration of skin irritation in a case in which ionic surfactants are used in the cosmetic.

Examples of nonionic surfactants include include glycerin fatty acid esters, organic acid monoglyceride, polyglycerin fatty acid esters, propylene glycol fatty acid esters, polyglycerin-condensed ricinoleate esters, sorbitan fatty acid esters, sucrose fatty acid esters and polyoxyethylene sorbitan fatty acid esters. These nonionic surfactants may be contained as oil phase components in the water-based cosmetic of the invention.

In a case in which the water-based cosmetic includes a nonionic surfactant, the content of nonionic surfactant is 1% by mass or lower, preferably 0.5% by mass or lower, and preferably 0.3% by mass or lower, relative to the total mass of the water-based cosmetic, from the viewpoint of forming finer dispersed particles.

In particular, the nonionic surfactant is preferably a polyglycerin fatty acid ester, and more preferably a polyglycerin fatty acid ester having HLB of from 10 to 16 (hereinafter sometimes referred to as "specific polyglycerin fatty acid ester"), from the viewpoint of emulsion stability. The polyglycerin fatty acid ester may be contained in the oil phase.

Surfactants such as specific polyglycerin fatty acid esters can drastically reduce the interfacial tension between the oil phase and the water phase, as a result of which the particle diameters of ceramidic compound-containing particles contained as an oil phase in the water-based cosmetic can be made smaller. Therefore, use of such surfactants is preferable.

Here, HLB is a hydrophilicity-hydrophobicity balance used usually in the field of surfactants, and a commonly-employed calculation formula, for example, the Kawakami formula can be used. In the invention, the Kawakami formula as shown below is employed.

$$HLB = 7 + 11.7 \log(M_w/M_o)$$

In the formula, $M_w$ represents the molecular weight of hydrophilic group(s) and $M_o$ is the molecular weight of hydrophobic group(s).

Numerical values of HLB provided in catalogs, etc. may also be used. Further, as can be seen from the formula, surfactants having desired HLB values can be obtained by utilizing the additive property of HLB.

Preferable polyglycerin fatty acid esters particularly preferably include at least one ester of a polyglycerin having an average polymerization degree of 10 and a fatty acid having from 8 to 18 carbon atoms such as capric acid, caprylic acid, lauric acid, myristic acid, palmitic acid, stearic acid, oleic acid or linoleic acid.

Preferable examples of the polyglycerin fatty acid ester include hexaglycerin monooleate, hexaglycerin monopalmitate, hexaglycerin monomyristate, hexaglycerin monolaurate, decaglycerin monooleate, decaglycerin monostearate, decaglycerin monopalmitate, decaglycerin monomyristate, decaglycerin monolaurate, etc. The HLBs thereof are preferably in a range of from 10 to 16.

Among them, more preferable examples include decaglycerin monolinoleate (HLB=12), decaglycerin monooleate (HLB=12), decaglycerin monostearate (HLB=12), decaglycerin monopalmitate (HLB=13), decaglycerin monomyristate (HLB=14), decaglycerin monolaurate (HLB=16), etc.

A most preferable polyglycerin fatty acid ester is decaglycerin oleate.

In the invention, these specific polyglycerin fatty acid esters may be used singly, or in combination of two or more thereof.

A surfactant selected from polyglycerin fatty acid esters having HLB of from 10 to 16, and a surfactant selected from polyglycerin fatty acid esters having a different molecular structure and having a HLB of from 5 to 15, may be used in combination as surfactants in the invention. The polyglycerin fatty acid ester having a HLB of from 5 to 15 may be a polyglycerin fatty acid ester encompassed by the polyglycerin fatty acid esters described above, or may be a polyglycerin fatty acid ester other than those polyglycerin fatty acid esters.

In the invention, it is preferable that a polyglycerin fatty acid ester in which the polymerization degree of glycerin is lower than 10 and the number of carbon atoms of the fatty acid thereof is from 12 to 18, and decaglycerin oleate, are contained as surfactants. The polyglycerin fatty acid ester in which the polymerization degree of glycerin is lower than 10 and the number of carbon atoms of the fatty acid thereof is from 12 to 18 is more preferably a polyglycerin fatty acid ester having a HLB of from 5.0 to 15 which is at least one selected from hexaglycerin fatty acid esters and tetraglycerin fatty acid esters.

Examples of hexaglycerin fatty acid esters and tetraglycerin fatty acid esters that can suitably be used in combination with the decaglycerin oleate include tetraglycerin monostearate (HLB=6), tetraglycerin monooleate (HLB=6), hexaglycerin monolaurate (HLB=14.5), hexaglycerin monomyristate (HLB=11), hexaglycerin monostearate (HLB=9) and hexaglycerin monooleate (HLB=9).

In a case in which decaglycerin oleate is used in combination with a hexaglycerin fatty acid ester and/or tetraglycerin fatty acid ester, the content ratio may be appropriately set in accordance with the application form of the ceramide dispersion. The ratio (decaglycerin fatty acid ester)/(tetraglycerin fatty acid ester and/or hexaglycerin fatty acid ester) is preferably in a range of from 1/0 to 1/1, more preferably to 1/0.5, and still more preferably to 1/0.25.

Commercial products may be applied as polyglycerin fatty acid esters such as specific polyglycerin fatty acid esters.

Commercial products of polyglycerin fatty acid esters include: NIKKOL DGMS, NIKKOL DGMO-CV, NIKKOL DGMO-90V, NIKKOL DGDO, NIKKOL DGMIS, NIKKOL DGTIS, NIKKOL TETRAGLYN 1-SV, NIKKOL TETRAGLYN 1-O, NIKKOL TETRAGLYN 3-S, NIKKOL TETRAGLYN 5-S, NIKKOL TETRAGLYN 5-O, NIKKOL HEXAGLYN 1-L, NIKKOL HEXAGLYN 1-M, NIKKOL HEXAGLYN 1-SV, NIKKOL HEXAGLYN 1-O, NIKKOL HEXAGLYN 3-S, NIKKOL HEXAGLYN 4-B, NIKKOL HEXAGLYN 5-S, NIKKOL HEXAGLYN 5-O, NIKKOL HEXAGLYN PR-15, NIKKOL DECAGLYN 1-L, NIKKOL DECAGLYN 1-M, NIKKOL DECAGLYN 1-SV, NIKKOL DECAGLYN 1-50SV, NIKKOL DECAGLYN 1-ISV, NIKKOL DECAGLYN 1-0, NIKKOL DECAGLYN 1-OV, NIKKOL DECAGLYN 1-LN, NIKKOL DECAGLYN 2-SV, NIKKOL DECAGLYN 2-ISV, NIKKOL DECAGLYN 3-SV, NIKKOL DECAGLYN 3-OV, NIKKOL DECAGLYN 5-SV, NIKKOL DECAGLYN 5-HS, NIKKOL DECAGLYN 5-IS, NIKKOL DECAGLYN 5-OV, NIKKOL DECAGLYN 5-O-R, NIKKOL DECAGLYN 7-S, NIKKOL DECAGLYN 7-O, NIKKOL DECAGLYN 10-SV, NIKKOL DECAGLYN 10-IS, NIKKOL DECAGLYN 10-OV, NIKKOL DECAGLYN 10-MAC AND NIKKOL DECAGLYN PR-20, which are manufactured by Nikko Chemicals Co., Ltd.; RYOTO POLYGLYESTER L-7D, L-10D, M-10D, P-8D, SWA-10D, SWA-15D, SWA-20D, S-24D, S-28D, O-15D, O-50D, B-70D, B-100D, ER-60D, LOP-120DP, DS13W, DS3, HS11, HS9, TS4, TS2, DL15 and DO13, which are manufactured by Mitsubishi-kagaku Foods Corporation; SUNSOFT Q-17UL, SUNSOFT Q-14S and SUNSOFT A-141C, which are manufactured by Taiyo Kagaku Co., Ltd.; and POEM DO-100 and POEM J-0021, which are manufactured by Riken Vitamin Co., Ltd.

Among those listed above, NIKKOL DECAGLYN 1-L, NIKKOL DECAGLYN 1-M, NIKKOL DECAGLYN 1-SV, NIKKOL DECAGLYN 1-50SV, NIKKOL DECAGLYN 1-ISV, NIKKOL DECAGLYN 1-O, NIKKOL DECAGLYN 1-OV AND NIKKOL DECAGLYN 1-LN, AND RYOTO POLYGLYESTER L-7D, L-10D, M-10D, P-8D, SWA-10D, SWA-15D, SWA-20D, S-24D, S-28D, O-15D, O-50D, B-70D, B-100D, ER-60D and LOP-120DP, are preferable.

Examples of other nonionic surfactants include other glycerin fatty acid esters, organic acid monoglycerides, polyglycerin fatty acid esters, propylene glycol fatty acid esters, polyglycerin-condensed ricinoleate esters, sorbitan fatty acid esters, sucrose fatty acid esters and polyoxyethylene sorbitan fatty acid esters. More preferable examples include sorbitan fatty acid esters, sucrose fatty acid esters and polyoxyethylene sorbitain fatty acid esters. These surfactants need not have been highly purified by distillation or the like, and may be a reaction mixture.

Sorbitan fatty acid esters of which the fatty acid has 8 or more carbon atoms are preferable, and sorbitan fatty acid esters of which the fatty acid has 12 or more carbon atoms are more preferable. Preferable examples of sorbitan fatty acid esters include sorbitan monocaprylate, sorbitan monolaurate, sorbitan monostearate, sorbitan sesquistearate, sorbitan tristearate, sorbitan isostearate, sorbitan sesquiisostearate, sorbitan oleate, sorbitan sesquioleate, and sorbitan trioleate.

In the invention, these sorbitan fatty acid esters may be used singly, or in combination of two or more thereof.

Examples of commercial products of sorbitan fatty acid esters include NIKKOL SL-10, SP-10V, SS-10V, SS-10MV, SS-15V, SS-30V, SI-10RV, SI-15RV, SO-10V, SO-15MV, SO-15V, SO-30V, SO-10R, SO-15R, SO-30R and SO-15EX, which are manufactured by Nikko Chemicals Co., Ltd.; SORGEN 30V, 40V, 50V, 90 and 110, which are manufactured by Daiichi Kogyo Seiyaku Co., Ltd.; and RHEODOL AS-10V, AO-10V, AO-15V, SP-L10, SP-P10, SP-S10V, SP-S30V, SP-O10V and SP-O30V, which are manufactured by Kao Corporation.

Sucrose fatty acid esters of which the fatty acid has 12 or more carbon atoms are preferable, and sucrose fatty acid esters of which the fatty acid has from 12 to 20 carbon atoms are more preferable.

Preferable examples of sucrose fatty acid esters include sucrose dioleate, sucrose distearate, sucrose dipalmitate, sucrose dimyristate, sucrose dilaurate, sucrose monooleate, sucrose monostearate, sucrose monopalmitate, sucrose monomyristate, sucrose monolaurate, etc. Among these, sucrose monooleate, sucrose monostearate, sucrose monopalmitate, sucrose monomyristate and sucrose monolaurate are more preferable.

In the invention, these sucrose fatty acid esters may be used singly, or in mixture.

Examples of commercial products of sucrose fatty acid esters include RYOTO SUGAR ESTER S-070, S-170, S-270, S-370, S-370F, S-570, S-770, S-970, S-1170, S-1170F, S-1570, S-1670, P-070, P-170, P-1570, P-1670, M-1695, O-170, O-1570, OWA-1570, L-195, L-595, L-1695, LWA-1570, B-370, B-370F, ER-190, ER-290 and POS-135, which are manufactured by Mitsubishi-kagaku Foods Corporation; and DK ESTER SS, F160, F140, F110, F90, F70, F50, F-A50, F-20W, F-10 and F-A10E, and COSMELIKE B-30, S-10, S-50, S-70, S-110, S-160, S-190, SA-10, SA-50, P-10, P-160, M-160, L-10, L-50, L-160, L-150A, L-160A, R-10, R-20, O-10 and O-150, which are manufactured by Daiichi Kogyo Seiyaku Co., Ltd.

Among them, RYOTO SUGAR ESTER S-1170, S-1170F, S-1570, S-1670, P-1570, P-1670, M-1695, O-1570 and L-1695, and DK ESTER SS, F160, F140 and F110, COSMELIKE S-110, S-160, S-190, P-160, M-160, L-160, L-150A, L-160A and O-150 are preferable.

Polyoxyethylene sorbitan fatty acid esters of which the fatty acid has 8 or more carbon atoms are preferable, and polyoxyethylene sorbitan fatty acid esters of which the fatty acid has 12 or more carbon atoms are more preferable. The length (addition mol number) of ethylene oxide units in the polyoxyethylene is preferably from 2 to 100, and more preferably from 4 to 50.

Preferable examples of polyoxyethylene sorbitan fatty acid esters include polyoxyethylene sorbitan monocaprylate, polyoxyethylene sorbitan monolaurate, polyoxyethylene sorbitan monostearate, polyoxyethylene sorbitan sesquistearate, polyoxyethylene sorbitan tristearate, polyoxyethylene sorbitan isostearate, polyoxyethylene sorbitan sesquiisostearate, polyoxyethylene sorbitan oleate, polyoxyethylene sorbitan sesquioleate, polyoxyethylene sorbitan trioleate, etc.

These polyoxyethylene sorbitan fatty acid esters may be used singly, or in mixture.

Commercial products of polyoxyethylene sorbitan fatty acid esters include NIKKOL TL-10, NIKKOL TP-10V, NIKKOL TS-10V, NIKKOL TS-10MV, NIKKOL TS-106V, NIKKOL TS-30V, NIKKOL TI-10V, NIKKOL TO-10V, NIKKOL TO-10MV, NIKKOL TO-106V and NIKKOL TO-30V, which are manufactured by Nikko Chemicals Co., Ltd.; RHEODOL TW-L106, TW-L120, TW-P120, TW-S106V, TW-S120V, TW-S320V, TW-O106V, TW-O120V, TW-O320V and TW-IS399C, and RHEODOL SUPER SP-L10 and TW-L120, which are manufactured by Kao Corporation; and SORGEN TW-20, TW-60V and TW-80V, which are manufactured by Daiichi Kogyo Seiyaku Co., Ltd.

1-5. Polymer Compound

The water-based cosmetic of the invention may include a polymer compound. Examples of the polymer compound include water-soluble polymer compounds, amphipathic polymers and non-water-soluble polymers.

Any of synthetic polymers, natural polymers and semi-synthetic polymers may widely be employed as water-soluble polymer compounds. In particular, sugars, proteins and complexes thereof are preferable.

Examples of sugars include, but are not limited to, monosaccharides, disaccharides, oligosaccharides, polysaccharides, dextrin, starch derivatives, gums, mucopolysaccharides, celluloses, etc.

Representative examples thereof include, but are not limited to, agarose, arabinose, amylose, amylopectin, gum acacia, gum arabic, arabinogalactan, alkylglycoside, alginic acid, sodium alginate, propyleneglycol alginate, aldose, inulin, oligosaccharides, ghatti gum, curdlan, carrageenan, galactomannan, galactose, xanthan gum, xylose, xyloglucan, chitin, chitosan, guar gum, cluster dextrin, β-glucan, glucuronic acid, glycogen, glycosaminoglycan, glyceraldehyde, glucosamine, glucose, glucomannan, ketose, chondroitin sulfate, Psyllium seed gum, gellan gum, cyclodextrin, sucrose, hydroxyethylcellulose, hydroxypropylcellulose, carboxymethylcellulose, methylcellulose, cellobiose, sorbitol, deoxyribose, dextrin, inverted sugar, starch, soy polysaccharides, sugar alcohols, glycoproteins, gum Tragacanth, trehalose, hyaluronic acid, fucose, fructose, pullulan, pectin, heparin, hemicellulose, maltose, mannitol, mannan, lactose, ribose, etc.

Among these sugars, gums and polysaccharides are preferable from the viewpoint of dispersion stability imparted by an increased viscosity, and xanthan gum, gum arabic, plullulan, etc. are more preferable from the viewpoint of the stability of carotenoids.

Any type of polymer or oligomer in which amino acid residues are polymerized via peptide bonds can be used as the protein. The protein is more preferably naturally-derived and water-soluble.

Proteins include simple proteins made from amino acids and conjugated proteins containing other components than amino acids, and both of them can be employed. Examples of simple proteins include gelatin, casein, fibroin, sericin, keratin, protamine, etc. Examples of conjugated proteins include: a glycoprotein, which is a protein attached to a hydrocarbon; a lipoprotein, which is a protein attached to a lipid; a metalloprotein, which is a protein attached to a metal ion; a nucleoprotein, which is a protein attached to a ribonucleic acid; a phosphoprotein, which is a protein attached to a phosphate group; etc.

In general, proteins are often named based on the source of proteins, examples of which include animal muscular proteins, milk proteins, egg proteins, rice proteins, wheat proteins (wheat gluten), soy proteins, yeast proteins, bacterial proteins, etc.

These proteins may be used in mixture.

It is also preferable to incorporate a polymer present in the skin, such as collagen, hyaluronic acid or ellastin, into the cosmetic.

The polymer compounds as described above may be used singly, or in combination of two or more thereof.

1-6. Water-Soluble Organic Solvent

The water-based cosmetic of the invention may include a water-soluble organic solvent. Water-soluble organic solvents are not included in the scope of "oil components" in the present specification.

The water-soluble organic solvent in the invention is contained in the oil phase that contains a natural ingredient, and is used for mixing with the later-described aqueous solution. The aqueous organic solvent is also a main component of an extraction liquid for extracting the natural ingredient. That is, the natural ingredient in the invention is mixed with the aqueous solution in a state in which the natural ingredient has been extracted into an extraction liquid of which the main component is a water-soluble organic solvent.

The term "water-soluble organic solvent" as used in the invention refers to an organic solvent having a solubility in water at 25° C. of 10% by mass or higher. The solubility in water is preferably 30% by mass or higher, and more preferably 50% by mass or higher, from the viewpoint of the stability of the resultant dispersion.

The water-soluble organic solvent may be used singly, or in the form of a mixed medium of plural water-soluble organic solvents. The water-soluble organic solvent may be used in the form of a mixture with water. In a case in which the mixture with water is used, it is preferable that the water-soluble organic solvent is contained in an amount of 50 vol. % or more, and more preferably 70 vol. % or more.

The water-soluble organic solvent is preferably used for preparing an oil phase by being mixed with oil phase components in the preparation of a ceramide dispersion in the later-described method of preparing a water-based cosmetic. The water-soluble organic solvent is preferably removed after mixing with the aqueous phase.

Examples of the water-soluble organic solvent include methanol, ethanol, 1-propanol, 2-propanol, 2-butanol, acetone, tetrahydrofuran, acetonitrile, methyl ethyl ketone, dipropylene glycol monomethyl ether, methyl acetate, methyl acetoacetate, N-methylpyrrolidone, dimethylsulfoxide, ethylene glycol, 1,3-butanediol, 1,4-butanediol, propylene glycol, diethylene glycol, triethylene glycol, etc., and mixtures thereof. Among them, for the application to foods, ethanol, propylene glycol or acetone is preferable, and ethanol or a mixed solution of ethanol and water is particularly preferable.

1-7. Other Components

Besides the components described above, in accordance with the application of the water-based cosmetic of the invention, other additives usually employed for the application, such as various medicinal ingredients, antiseptic agents and coloring agents, may further be used in the water-based cosmetic as long as the effects of the invention are not impaired.

Examples of such other additives include: moisturizing agents, such as glycine betain, xylitol, trehalose, urea, neutral amino acids and basic amino acids; medicinal agents such as allantoin; organic powders such as cellulose powder, nylon powder, crosslinked silicone powder, crosslinked methylpolysiloxane, porous cellulose powder and porous nylon powder; inorganic powders such as anhydrous silica, zinc oxide and titanium oxide; algefacients such as menthol and camphor; plant extracts; pH buffering agents; antioxidants; UV absorbers; UV scattering agents; antiseptics; flavoring agents; antibacterial agents; and colorants.

In a case in which the ceramidic compound-containing particles are used together with other oil components to form the oil phase in the water-based cosmetic of the invention, the particle diameter of dispersed particles contained as the oil phase can be controlled by factors attributable to the components contained in the water-based cosmetic, as well as by factors such as agitation conditions (shear force, temperature, pressure) or micromixer operation conditions of the later-described ceramide dispersion production method, and the ratio between the oil phase and the aqueous phase, whereby desired atomized oil phase particles of 150 nm or less can be obtained.

The transparency of the water-based cosmetic of the invention can roughly be assessed by visual observation of the appearance thereof. However, in general, the transparency can be assessed by the turbidity of the water-based cosmetic. The turbidity of the water-based cosmetic can be measured as an absorbance at 660 nm and 25° C. using a UV-VIBLE spectrophotometer UV-2550 (manufactured by Shimadzu Corporation) and a 10 mm cell. The water-based cosmetic of the invention is assessed as transparent if the result of this measurement based on the absorbance at 660 nm is 0.050 or less. The transparency of the water-based cosmetic is preferably such that the absorbance is 0.040 or less.

The pH of the water-based cosmetic of the invention is preferably from 5 to 9, and more preferably from 6 to 8.5. A water-based cosmetic having excellent dispersion stability and storage stability can be obtained by setting the pH of the water-based cosmetic to be within the range described above. Various pH adjusters may be used in order to adjust the pH of the water-based cosmetic to be within this range.

In the production process of the water-based cosmetic, a pH adjuster may be added and mixed during the preparation of the oil phase or the aqueous phase so as to set the pH to be within a predetermined range, or may be added directly to the water-based cosmetic obtained. Usable pH adjusters include various inorganic salts usually employed in this field, including acids such as hydrochloric acid and phosphoric acid and alkalis such as sodium hydroxide, and buffering agents such as lactic acid—sodium lactate, citric acid—sodium citrate, and succinic acid—sodium succinate.

2. Production Method of Water-Based Cosmetic

The water-based cosmetic of the invention may be produced by any method, as long as the water-based cosmetic includes a fatty acid or a salt thereof, ceramidic compound-containing particles dispersed as an oil phase component in an aqueous phase, and the aqueous phase including at least the polyhydric alcohol component.

From the viewpoint of forming fine ceramidic compound-containing particles with excellent solution stability, one of preferable methods for producing the water-based cosmetic of the invention is a method including: preparing, in advance, a ceramide dispersion that contains (i) a fatty acid or a salt thereof and (ii) ceramidic compound-containing particles dispersed as an oil phase in an aqueous phase; and mixing the ceramide dispersion with an aqueous composition containing other essential components or optional components. Here, the polyhydric alcohol component may be added as an aqueous phase component during the production of the ceramide dispersion, or may be added to the aqueous phase of the ceramide dispersion obtained. It is also possible to add the polyhydric alcohol component, in portions, to both of these stages.

In a case in which this method is adopted, the aqueous composition may be an aqueous solution containing an aqueous medium, such as water, as the main component, and may be configured to contain the natural polysaccharide, the polyhydric alcohol, etc. The aqueous composition may be selected, as appropriate, in consideration of the aqueous phase components of the ceramide dispersion.

The mixing ratio of the ceramide dispersion and the aqueous composition may be any mixing ratio as long as the contents of the components discussed above are within their respective ranges of contents mentioned for the water-based cosmetic. In general, the mixing ratio of the ceramide dispersion and the aqueous composition is preferably in a range of from 1:0.1 to 1:10,000, and more preferably in a range of from 1:0.1 to 1:1,000.

In the following, the ceramide dispersion that can be used in the preferable production method of the water-based cosmetic of the invention is described in further detail.

(Ceramide Dispersion)

The ceramide dispersion prepared for the production of the water-based cosmetic is a transparent ceramide dispersion that contains ceramidic compound-containing particles dispersed, as an oil phase, in the aqueous phase, and a fatty acid component, which is an oil phase component or an aqueous phase component. The ceramide dispersion can be obtained according to a production method that includes mixing aqueous phase components and oil phase components including at least a ceramidic compound, at a temperature of 40° C. or lower.

According to this method, a ceramide dispersion having excellent stability over time and excellent storage stability can be obtained since the oil phase components are dissolved well due to the oil phase components and the aqueous phase components being mixed at a temperature of 40° C. or lower.

The above-described water-soluble organic solvent for dissolving ceramidic compounds can preferably be used for the preparation of the oil phase. Examples of the water-soluble organic solvent to be used for this purpose include all of those listed above.

The temperature at the time of mixing the oil phase components and the aqueous phase components in the preparation of the ceramide dispersion is 40° C. or lower. The temperature of 40° C. or lower at the time of mixing should be achieved at the time of mixing the oil phase components and the aqueous phase components, and the extent to which this temperature setting is applied may be varied in accordance with the mixing (emulsification) method applied. In the case of a method using a micromixer, the temperature in at least a region from directly before mixing to directly after dispersion should be set to be 40° C. or lower.

Known methods, such as a high-pressure emulsification method of applying a shear force of 100 MPa or greater or a jet injection method of directly injecting the oil phase components into the aqueous phase components, may be employed for the mixing of the aqueous phase components and the oil phase components.

From the viewpoints of the particle diameter, dispersion stability and storage stability of the ceramidic compound-containing particles, it is preferable to employ a method using a micromixer, which includes passing the oil phase components and the aqueous phase components, independently of each other, through microchannels of which narrowest portion has a cross-sectional area of from 1 μm$^2$ to 1 mm$^2$, and thereafter combining and mixing them.

Here, the viscosity of the aqueous phase is preferably 30 mPa·s or less from the viewpoint of decreasing the sizes of the ceramidic compound-containing particles.

An example of a method of producing the ceramide dispersion includes steps of:

a) preparing an aqueous phase using an aqueous medium (such as water) that contains a fatty acid salt (if any);

b) preparing an oil phase using oil phase components, including at least a ceramidic compound;

c) mixing and dispersing the oil phase and the aqueous phase according to the method detailed below, using a micromixer, to form a ceramide dispersion (emulsion) that contains ceramidic compound-containing particles (dispersed particles) having a volume average particle diameter of from 1 nm to 100 nm.

The ratio of the oil phase to the aqueous phase (by mass) in the emulsification/dispersion is not particularly limited, and the oil phase/aqueous phase ratio (% by mass) is preferably in a range of from 0.1/99.9 to 50/50, more preferably from 0.5/99.5 to 30/70, and still more preferably from 1/99 to 20/80.

An oil phase/aqueous phase ratio within the above range is preferable since a sufficient amount of active ingredient is contained, and practically sufficient emulsion stability can be obtained.

In a case in which it is desired to obtain a powdery composition using the ceramide dispersion, the powdery composition can be obtained by further adding a step of drying the thus-obtained ceramide composition in the emulsion state by, for example, spray drying.

The components contained in the oil phase and the aqueous phase in the production method of the ceramide dispersion are the same as the constituent components of the above-described ceramide dispersion of the invention, and preferable examples and preferable amounts thereof are also the same, and preferable combinations thereof are also the same.

(Micromixer)

In the production method applied to the production of the ceramide dispersion, it is preferable to employ a production method that includes passing the oil phase components and the aqueous phase components, independently of each other, through microchannels of which narrowest portion has a cross-sectional area of from 1 μm$^2$ to 1 mm$^2$, and thereafter combining and mixing them, in order to form ceramidic compound-containing particles having a volume average particle diameter of from 1 nm to 100 nm in a stable manner.

The mixing of the oil phase components and the aqueous phase components is preferably mixing by counter-flow collision, from the viewpoint of obtaining finer dispersed particles.

An apparatus most preferable for mixing by counter-flow collision is a counter collision micromixer. A micromixer is generally a device which mixes two different liquids in a microspace, one of the liquids is an organic solvent phase containing a functional oil component, and the other liquid is an aqueous phase which is an aqueous solution.

Application of a micromixer to preparation of an emulsion having a small particle diameter, which is a microchemical process, exhibits relatively low energy consumption, generates less heat, and enables provision of an emulsion or dispersion that has substantially uniform particle diameters and has excellent storage stability compared to usual agitation emulsification dispersing methods or high-pressure homogenizer emulsification dispersing. The application of a micromixer is a most suitable method for emulsification in a case in which a natural ingredient that is susceptible to thermal deterioration is contained.

In summary, an emulsification or dispersing method using a micromixer includes distributing the aqueous phase and the oil phase to microspaces, and contacting or colliding them in the respective microspaces. Known micromixers include two kinds of methods: a method in which mixing is carried out while maintaining a laminar flow, and a method in which mixing is carried out while disturbing a flow, that is, in a turbulent flow. Either method may be employed. The method using a turbulent flow is preferable from the viewpoints of stability and transparency. Examples of micromixers using a turbulent flow include slit-interdigital-type micromixers (such as those manufactured by IMM Gmbh) and collision-type micromixers (such as KM mixers).

In a case in which emulsification is carried out by micro-mixing using a collision-type micromixer in the invention, in regard to the temperature at the emulsification (emulsification temperature), the micro-mixing is preferably carried out in such a manner that the temperature of the aforementioned separate microspaces of the micromixer (the temperature at micro-mixing part of the micromixer) is 40° C. or lower, preferably from 0° C. to 40° C., and particularly preferably from 5° C. to 30° C., from the viewpoint of uniformity of the particle diameters in the resulting emulsion. An emulsification temperature of 0° C. or higher is preferable since a main component of the dispersing medium is water and, therefore, the emulsification temperature can be controlled. The temperature of the microspaces of the micromixer is preferably maintained at 40° C. or lower. By maintaining the temperature at 40° C. or lower, management of the maintained temperature can easily be controlled, and the micro-bumping phenomenon which adversely influences the emulsification performance can be prevented. The maintained temperature is further preferably controlled at a temperature of 35° C. or lower.

In the invention, after micro-mixing and emulsification are carried out with the temperatures at which the aqueous phase and the oil phase before and after being distributed to the microspaces of the micromixer and the temperatures at which the microspaces and the separate microspaces of the micromixer are maintained being adjusted to temperatures higher than room temperature, the oil-in-water emulsion obtained using the micromixer is preferably cooled to room temperature after recovery.

The cross-sectional area of the narrowest part of the microspaces (flow channels) of the micromixer in the invention is from 1 µm² to 1 mm², and, from the viewpoints of decreasing the emulsion particle diameter and narrowing the particle diameter distribution, the cross-sectional area is preferably from 500 µm² to 50,000 µm².

The cross-sectional area of the narrowest part of the microspaces (flow channels) for the aqueous phase in the micromixer in the invention is particularly preferably from 1,000 µm² to 50,000 µm² from the viewpoint of stability of mixing.

The cross-sectional area of the narrowest portion of the microspaces (flow channels) for the oil phase in the micromixer is particularly preferably from 500 µm² to 20,000 µm² from the viewpoints of decreasing the emulsion particle diameter and narrowing the particle diameter distribution.

In the case of mixing (emulsifying and dispersing) using the micromixer, the flow rates of the oil phase and the aqueous phase in emulsification and dispersion varies depending on the micromixer used. The flow rate of the aqueous phase is preferably from 10 ml/min to 500 ml/min, more preferably from 20 ml/min to 350 ml/min, and particularly preferably from 50 ml/min to 200 ml/min, from the viewpoints of decreasing the emulsion particle diameter and narrowing the particle diameter distribution.

The flow rate of the oil phase is preferably from 1 ml/min to 100 ml/min, more preferably from 3 ml/min to 50 ml/min, and particularly preferably from 5 ml/min to 50 ml/min, from the viewpoints of decreasing the emulsion particle diameter and narrowing the particle diameter distribution.

The ratio between the values obtained by dividing the flow rates of both phases by the respective microchannel cross-sectional areas, that is, the ratio between the flow speeds of both phases (Vo/Vw) is preferably in the range from 0.05 to 5 from the viewpoints of forming finer particles and the design of the micromixer. Here, Vo represents the flow speed of an organic solvent phase containing a water-insoluble natural integrant, and Vw represents the flow speed of an aqueous phase. Furthermore, a flow speed ratio (Vo/Vw) is most preferably in the range of is from 0.1 to 3 from the viewpoint of forming still finer particles.

In regard to the liquid feed pressures for the aqueous phase and the oil phase, the liquid feed pressure for the aqueous phase and the liquid feed pressure for the oil phase are preferably from 0.030 MPa to 5 MPa and from 0.010 MPa to 1 MPa, respectively, and more preferably from 0.1 MPa to 2 MPa and 0.02 MPa to 0.5 MPa, respectively, and particularly preferably from 0.2 MPa to 1 MPa and from 0.04 MPa to 0.2 MPa, respectively. A liquid feed pressure for the aqueous phase of from 0.030 MPa to 5 MPa is preferable since a stable liquid feed rate tends to be maintained. A liquid feed pressure for the oil phase of from 0.010 MPa to 1 MPa is preferable, since uniform mixing tends to be achieved.

In the production method that can be applied to the production of the ceramide dispersion, the water-soluble organic solvent used is preferably removed after the emulsification or dispersion using microchannels. Examples of the methods of removing the solvent include an evaporation method using a rotary evaporator, a flash evaporator, an ultrasound atomizer or the like, and a membrane separation method using an ultrafiltration membrane, a reverse osmosis membrane or the like. An ultrafiltration membrane method is particularly preferable.

An ultra filter (UF) is an apparatus with which an original solution (a mixed aqueous solution of water, a high-molecular substance, a low-molecular substance, a colloidal substance, etc.) that is pressurized and injected thereto is separated into two solutions—a filtrate (the low-molecular substance) and a concentrate liquid (the high-molecular substance or colloidal substance)—, which can be taken out therefrom.

An ultrafiltration membrane is a typical asymmetric membrane produced by the Loeb-Sourirajan method. Examples of polymer materials used therefor include polyacrylonitrile, polyvinyl chloride—polyacrylonitrile copolymer, polysulfone, polyether sulfone, vinylidene fluoride, aromatic polyamide, cellulose acetate, etc. In recent years, ceramic membranes have also been employed. Different from the reverse osmosis method etc., no pre-treatment is carried out in the ultrafiltration method. Therefore, fouling—deposition of polymers etc. on the membrane surface—occurs. For this reason, it is a common practice to wash the membrane with a chemical or hot water at regular intervals. Thus, the membrane material should be resistant to chemicals and heat. There are various types of membrane modules for ultrafiltration membranes, such as a flat membrane type, a tubular type, a hollow fiber type and a spiral type. The performance indicator of ultrafiltration membranes is a molecular weight cut off, and various membranes having molecular weight cut off values of from 1,000 to 300,000 are commercially available. Examples of commercially available membrane modules include, but are not limited to, MICROZA UF (Asahi Kasei Chemicals Corporation), capillary-type element NTU-3306 (Nitto Denko Corporation), etc.

For the removal of solvents from the emulsion obtained, the material of the membrane is particularly preferably polysulfone, polyether sulfone or aromatic polyamide, from the viewpoint of resistance to solvents. In regard to the form of the membrane module, flat membranes are mainly employed on the laboratory scale, while membranes of the hollow fiber type and spiral type are employed industrially, of which hollow fiber type membranes are particularly preferable. Although the molecular weight cut off varies depending on the kind of active ingredient, the molecular weight cut off is usually in the range of from 5,000 to 100,000.

Although an operation temperature of from 0° C. to 80° C. is possible, a temperature range of from 10° C. to 40° C. is particularly preferable in consideration of the degradation of active ingredients.

Examples of laboratory-scale ultrafiltration apparatuses include ADVANTEC-UHP (ADVANTEC) and a flow-type labo-test unit RUM-2 (Nitto Denko Corporation), which employ flat membrane-type modules. For industrial applications, a plant may be constructed by combining the respective membrane modules in any number and any size in accordance with the required performance. Further, RUW-5A (Nitto Denko Corporation), etc. are commercially available as bench-scale units.

In the production method that can be applied to the ceramide dispersion of the invention, a process of concentrating the resultant emulsion, which follows the solvent removal, may be added. For the concentration method, the same methods and devices as those employed for the removal of solvent, such as the evaporation method and the filtration method, may be used. The ultra-filtration membrane method is preferable also in the case of the concentration. Although it is preferable to use, if possible, the same membrane as in the solvent removal, a ultrafiltration membrane having a molecular weight cut off different from that of the membrane used for the solvent removal may be used, as necessary. It is also possible to run the apparatus at a different temperature from that of the solvent removal, so as to increase the concentration efficiency.

The ceramide dispersion obtained by the mixing using a micromixer is an oil-in-water emulsion. In the invention, the volume average particle diameter (median diameter) of the ceramidic compound-containing particles contained in the ceramide dispersion is from 2 nm to 150 nm. From the viewpoint of the transparency of the dispersion obtained, the volume average particle diameter is more preferably from 5 nm to 50 nm. The particle diameter of the ceramidic compound-containing particles (dispersed particles) can be measured using, for example, a commercially available particle size analyzer, and the details thereof are as described above.

3. Application of Water-Based Cosmetic

The cosmetic of the invention may have any general formulation form known as a cosmetic, such as a skin lotion, a serum, a gel, a milky lotion and a facial wash. In order to enjoy the benefit of a small particle diameter of the ceramidic compound-containing particles of the invention, the cosmetic preferably has a formulation form with high transparency, and is preferably a skin lotion, a serum or a gel formulation.

EXAMPLES

The invention is describe in further detail below by way of examples. However, the invention is not limited to the examples below as long as the gist of the invention is retained. Further, "%" and "part" are based on mass, unless specified otherwise.

Example 1

(Preparation-1 of Ceramide Dispersion)

The ingredients listed in the following oil phase liquid 1 composition were agitated at room temperature for about 30 minutes, thereby preparing oil phase liquid 1.

For the preparation of aqueous phase liquid 1, the compounds listed in the following aqueous phase liquid 1 composition were added to the pure water, and heated to about 50° C., and sufficiently dissolved by agitation. Thereafter, the remaining ingredients were added thereto and mixed, and the liquid temperature was adjusted to 30° C.

<Oil Phase Liquid 1 Composition>

| Ceramide 3B [Natural Ceramide] | 0.9 parts |
|---|---|
| Ceramide 6 [Natural Ceramide] | 1.1 parts |
| Oleic acid (Melting Point: 14° C.) | 0.4 parts |
| Ethanol (Water-soluble Organic Solvent) | 97.6 parts |

<Water Phase Liquid 1 Composition>

| Pure Water | 97.14 parts |
|---|---|
| Glycerin | 1.43 parts |
| 1,3-butylene glycol | 1.43 parts |
| Sodium hydroxide | Appropriate amount |

The resultant oil phase liquid 1 (oil phase) and aqueous phase liquid 1 (aqueous phase) were subjected to micromixing in a ratio of 1:7 (ratio by mass), using a collision-type KM micromixer 100/100, as a result of which ceramide dispersion liquid 1 at 30° C. was obtained. The usage conditions of the micromixer were as follows.

—Microchannel—

Oil Phase-Side Microchannel:

cross-sectional shape/width/depth/length=rectangular shape/70 μm/100 μm/10 mm

Aqueous Phase-Side Microchannel:

cross-sectional shape/width/depth/length=rectangular shape/490 μm/100 μm/10 mm

—Flow Rates—

Micro-mixing was carried out while introducing the aqueous phase to the outer annular channel at a flow rate of 21.0 ml/min., and introducing the oil phase to the inner annular channel at a flow rate of 3.0 ml/min.

Ceramide dispersion liquid 1 obtained was repeatedly subjected to solvent removal using an EVAPOR (CEP-lab) manufactured by Okawara Mfg. Co., Ltd., until the ethanol concentration became 0.1% by mass or lower, so that the ceramide dispersion liquid was concentrated and adjusted to have a ceramide concentration of 2.0% by mass, as a result of which ceramide dispersion A having a pH of 7.5 was obtained. Here, the ceramide concentration is the content of ceramidic compounds relative to the total mass of the ceramide dispersion.

(Preparation of Water-Based Cosmetic)

The ingredients shown in Table 1 other than the ceramide dispersion, including the first polyhydric alcohol and the second polyhydric alcohol, were mixed and dissolved at room temperature in such amounts that the amounts of the respective components in the water-based cosmetic after preparation would be the amounts shown in Table 1. Thereafter, water as the remaining part was added to adjust the total amount to 100 parts by mass, whereby water-based cosmetic A was obtained.

Example 2

In Example 2, ceramide dispersion B was obtained in the same manner as in Example 1, except that the preparation of the ceramide dispersion was carried out in the following manner.

Specifically, the preparation of oil phase liquid 1 and aqueous phase liquid 1 was carried out in the same manner as in Example 1. Aqueous phase liquid 1 obtained was stirred by a stirrer, oil phase liquid 1 was slowly added dropwise, whereby water-based cosmetic B at 30° C. was obtained.

Examples 3 to 6

In Examples 3 to 5, ceramide dispersions C to F were prepared, and then water-based cosmetics C to F were obtained, in the same manner as in Example 1, except that the final concentrations of the respective ingredients in the water-based cosmetic were changed as shown in Table 1.

Comparative Example 1 and Comparative Example 2

Ceramide dispersions G and H were obtained in the same manner as in Example 1 and Example 2, respectively, except that 0.4 parts of polyglycerin fatty acid ester were used in place of the 0.4 parts of oleic acid; then, water-based cosmetics G and H were obtained therefrom, in the same manner as in Example 1. The polyglycerin fatty acid ester employed here was polyglyceryl-10 oleate (HLB=12.0).

Comparative Examples 3 to 8

In Comparative Examples 3 to 8, ceramide dispersions I to N were obtained, and water-based cosmetics I to N were obtained, in the same manner as in Example 1, except that the final concentrations of the respective ingredients in the water-based cosmetic were changed as shown in Table 1.

<Evaluation>

1. Particle Diameter of Ceramidic Compound-Containing Particles

The particle diameter of the ceramidic compound-containing particles (or dispersed particles in the form of oil-droplets containing the same) in each water-based cosmetic directly after the preparation thereof was measured using a dynamic light scattering particle size analyzer LB-550 (manufactured by HORIBA Ltd.). The measurement of the particle diameter was carried out using a quartz cell, after diluting the water-based cosmetic with pure water so as to set the concentration of the ceramidic compound-containing particles to 1% by mass. The particle diameter was determined as the volume average particle diameter with the following settings:

sample refractive index: 1.600
dispersion medium refractive index: 1.333 (pure water)
viscosity of dispersion medium: the viscosity of pure water.

2. Evaluation of Ceramide Permeation Properties

The permeation properties of the ceramide dispersion into the stratum corneum were evaluated with respect to adult men and women (3 men and 2 women). Application to an upper arm portion in an amount of 80 mg/6 cm$^2$ per time was carried out twice a day (in the morning and in the evening). After the application was carried out for one week, the applied portion was washed using soap, and tape stripping was carried out on the applied portion. After 5 layers were stripped off, the matter adhered to each tape was extracted using ethanol, and the ceramide amount was quantified using LC-MS. Based on the quantified ceramide VI amount, the permeation properties into the stratum corneum was evaluated according to the following criterion.

The evaluation was carried out based on the permeation amount of each water-based cosmetic, assuming that the permeation amount of the water-based cosmetic of Comparative Example 2 is 1.0. The results are shown in Table 1 below. In the Table, "-" means that the permeation properties could not be evaluated due to inferior stability.

A: 8.0 or more
B: 2.0 or more
C: less than 2.0

Further, from among the water-based cosmetics ranked C in the evaluation of ceramide permeation properties, those having greatly inferior ceramide permeation properties (1.0 or less) were ranked D.

3. Evaluation of Moisturized Feeling

Each water-based cosmetic prepared was evaluated by 10 women with respect to moisturized feeling. The water-based cosmetic was applied to a forearm portion in an amount of about 0.2 g, and the feeling after use was evaluated according to the following criterion. The results are shown in Table 1 below.

A: Sufficient Moisturized Feeling
B: Moisturized Feeling
C: No Moisturized Feeling 4. Evaluation of Stability Over Time of Water-Based Cosmetic The evaluation of the stability over time was carried out according to the following method, based on turbidity.

The turbidity of each of the water-based cosmetics of Examples 1 to 5 and Comparative Examples 1 to 7 directly after the preparation thereof was measured as the absorbance at 660 nm (measurement temperature: 25° C.), using a UV-VIBLE spectrophotometer UV-2550 (manufactured by Shimadzu Corporation) and a 10 mm quartz cell.

Further, each water-based cosmetic was stored in a constant-temperature bath at 60° C. for 24 hours, and stored in a refrigerator at 4° C. for another 24 hours. This cycle was repeated, so that 7 cycles (2 weeks) in total were carried out. Thereafter, the water-based cosmetic was returned to 25° C., and the turbidity was measured again.

The difference between the turbidity after the storage over time and the turbidity directly after the preparation was calculated as a change in turbidity of each water-based cosmetic, and was evaluated according to the following criterion. The results are shown in Table 1 below.

A: turbidity change of less than 0.05 (although a turbidity changes is noticeable, the change is at a level that poses no problem on the commercial value as cosmetic)
B: turbidity change of from 0.05 to less than 0.1 (at a level that is barely acceptable in terms of commercial value as cosmetic)
C: turbidity change of 0.1 or more (at a level that has no commercial value as cosmetic)

Further, from among the water-based cosmetics ranked C with respect to the stability over time, those having greatly inferior stability over time (turbidity change of 0.3 or more) are ranked D.

TABLE 1

| | Examples | | | | | | Comparative Examples | | | | | | | |
|---|---|---|---|---|---|---|---|---|---|---|---|---|---|---|
| | 1 | 2 | 3 | 4 | 5 | 6 | 1 | 2 | 3 | 4 | 5 | 6 | 7 | 8 |
| Ceramide IIIB, VI mixture | 1.00% | 1.00% | 1.00% | 1.00% | 1.00% | 1.00% | 1.00% | 1.00% | 1.00% | 1.00% | 1.00% | 1.00% | 1.00% | 1.00% |
| Oleic Acid | 0.20% | 0.20% | 0.20% | 0.20% | 0.20% | 0.20% | | | 0.20% | 0.20% | 0.20% | 0.20% | 0.50% | 0.20% |
| Polyglycerin fatty acid ester (HLB = 12) | | | | | | | 0.20% | 0.20% | | | | | | |
| Sodium hydroxide | Suitable amount | Suitable amount | Suitable amount | Suitable amount | Suitable amount | Suitable amount | Suitable amount | Suitable amount | Suitable amount | Suitable amount | Suitable amount | Suitable amount | Suitable amount | Suitable amount |
| Phosphate buffer | Suitable amount | Suitable amount | Suitable amount | Suitable amount | Suitable amount | Suitable amount | Suitable amount | Suitable amount | Suitable amount | Suitable amount | Suitable amount | Suitable amount | Suitable amount | Suitable amount |
| Methylparaben | 0.20% | 0.20% | 0.20% | 0.20% | 0.20% | 0.20% | 0.20% | 0.20% | 0.20% | 0.20% | 0.20% | 0.20% | 0.20% | 0.20% |
| Glycerin (IOB = 5.0) | 5.00% | 5.00% | 4.00% | | 5.00% | 10.00% | 5.00% | 5.00% | | 5.00% | 2.00% | | 5.00% | 15.00% |
| BG (IOB = 2.5) | 5.00% | 5.00% | 4.00% | 4.00% | | 10.00% | 5.00% | 5.00% | 2.00% | | | | 5.00% | 15.00% |
| Pentylene glycol (IOB = 2.0) | | | 2.00% | | | | | | | | 4.00% | 2.00% | | |
| Hexylene glycol (IOB = 1.82) | | | | | 1.00% | | | | | | | | | |
| Water | Balance | Balance | Balance | Balance | Balance | Balance | Balance | Balance | Balance | Balance | Balance | Balance | Balance | Balance |
| pH | 7.5 | 7.5 | 7.5 | 7.5 | 7.5 | 7.5 | 7.5 | 7.5 | 7.5 | 7.5 | 7.5 | 7.5 | 7.5 | 7.5 |
| Particle diameter (nm) | 10 nm | 150 nm | 10 nm | 10 nm | 10 nm | 10 nm | 10 nm | 150 nm | 10 nm | 10 nm | 10 nm | 10 nm | 100 nm | 10 nm |
| Ceramide permeation properties | 8.7 A | 4.7 B | A | A | A | A | 1.3 C | 1.0 D | — | — | — | — | — | — |
| Moisturized feeling | A | A | A | B | A | B | A | A | A | A | B | C | A | A |
| Stability over time | A | A | B | A | B | B | A | A | C | C | C | C | C | D |

As demonstrated in Table 1, it is understood that the water-based cosmetics of the Examples, which contain a fatty acid component and contain a polyhydric alcohol or polyhydric alcohols having IOB of 2.2 or higher at 3% by mass or more, are excellent in terms of all of the ceramide permeation properties, the moisturized feeling and the stability over time.

In particular, the water-based cosmetic of Examples which contain no or only a very small amount of second polyhydric alcohol having IOB of 2.0 or less exhibit further improved stability over time.

The disclosures of Japanese Patent Application No. 2010-089059 and Japanese Patent Application No. 2011-054511 are incorporated herein by reference in their entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A method of producing a water-based cosmetic comprising:
   (A) ceramidic compound-containing particles that include a ceramidic compound and that are dispersed as an oil phase in an aqueous phase;
   (B) a fatty acid component composed of at least one selected from the group consisting of fatty acids and fatty acid salts; and
   (C) a polyhydric alcohol component that includes a first polyhydric alcohol having an IOB of 2.2 or more and a total content in the water-based cosmetic of from 3% by mass to 20% by mass, and a second polyhydric alcohol having an JOB of 2.0 or less and a total content in the water-based cosmetic of 0% by mass or not more than 3% by mass, wherein the ceramidic compound is selected from the group consisting of ceramide 1, ceramide 9, ceramide 4, ceramide 2, ceramide 3, ceramide 5, ceramide 6, ceramide 7, ceramide 8 and ceramide 3B, the fatty acid component is selected from the group consisting of lauric acid, oleic acid, isostearic acid α-linolenic acid, γ-linolenic acid, and salts thereof, the first polyhydric alcohol is selected from the group consisting of propylene glycol, glycerin, and 1,3-butyleneglyco-diglycerin, the second polyhydric alcohol is selected from the group consisting of isoprene glycol, dipropylene glycol, ethoxy diglycol (diethylene glycol monoethyl ether), penthylene glycol, and hexylene glycol, and the total content of surfactant in the water-based cosmetic is 0% by mass or not more than 1% by mass, and the total mass of the ceramidic compound in the water-based cosmetic is at least 3.0 times the total mass of the fatty acid component, said method comprising the steps of:
   mixing an oil phase component that includes at least a ceramidic compound, and an aqueous phase component, at a temperature of 40° C. or lower, to obtain a ceramide dispersion that includes a polyhydric alcohol component in the aqueous phase component; and
   mixing the ceramide dispersion and an aqueous composition.

2. The method of producing a water-based cosmetic according to claim 1, wherein the polyhydric alcohol component is added as one component in the aqueous phase component when the oil phase component and the aqueous phase component are mixed, or the polyhydric alcohol component is added to a ceramide dispersion liquid obtained after the mixing.

3. The method of producing a water-based cosmetic according to claim 1, further comprising dissolving the ceramidic compound in a solvent.

4. The method of producing a water-based cosmetic according to claim 1, wherein the oil phase component and the aqueous phase component are each independently passed through a microchannel of which a cross-sectional area of a narrowest part thereof is from 1 $\mu m^2$ to 1 $mm^2$, and are thereafter combined and mixed with each other.

5. The method of producing a water-based cosmetic according to claim 1,
　　wherein the ceramidic compound comprises two or more natural ceramides.

\* \* \* \* \*